United States Patent [19]

Hehrlein et al.

[11] Patent Number: 5,674,177
[45] Date of Patent: Oct. 7, 1997

[54] VASCULAR IMPLANT

[75] Inventors: Christoph Hehrlein, Heidelberg; Peter Fehsenfeld, Stutensee, both of Germany

[73] Assignee: Kernforschungszentrum Karlsruhe GmbH, Karlsruhe, Germany

[21] Appl. No.: 503,374

[22] Filed: Jul. 17, 1995

Related U.S. Application Data

[63] Continuation-in-part of PCT/EP94/01373, Apr. 24, 1994.

[30] Foreign Application Priority Data

May 6, 1993 [DE] Germany .................. 42 15 002.0

[51] Int. Cl.$^6$ ........................................ A61N 5/00
[52] U.S. Cl. ........................................ 600/3
[58] Field of Search ............................. 600/1–8

[56] References Cited

U.S. PATENT DOCUMENTS 3,750,653  8/1973  Simon .
4,706,652  11/1987  Horowitz .
5,199,939  4/1993  Dake et al. .

FOREIGN PATENT DOCUMENTS 0433011  6/1991  European Pat. Off. .
0497495  8/1992  European Pat. Off. .
0539165  4/1993  European Pat. Off. .
9203179  3/1992  WIPO .
9304735  3/1993  WIPO .

*Primary Examiner*—John P. Lacyk
*Attorney, Agent, or Firm*—Klaus J. Bach

[57] ABSTRACT

In a vascular implant for the prevention or elimination of vascular restrictions a tubular body to be inserted into a body vessel includes at least a first nuclide species which has a half life in the range of 7 hours to 7 days and a second nuclide species which has a half life of more than 100 days. Instead of providing a second nuclide species, the first nuclide species may also decay into the second nuclide species thereby providing a high initial radioactivity for a relatively short period and a relatively low radioactivity over a relatively long period.

3 Claims, No Drawings

VASCULAR IMPLANT

This is a continuation-in-part-application of International patent application PCT/EP94/01373 filed Apr. 29, 1994 claiming the priority of the German patent application P 43 15 002.0 of May 6, 1993.

BACKGROUND OF THE INVENTION

1. Field of the Invention

The present application resides in a vascular implant including radio nuclides which subject the tissues adjacent to the implant to radioactive radiation to avoid restenosis.

2. Description of the Prior Art

Vascular implants, so-called stents, are utilized in the medicine to prevent or eliminate vascular restrictions. The implants may be inserted into a restricted vessel whereby the restricted vessel is widened. The vascular implants have, for example, the shape of net-like tubes or coil springs.

The experience with such vascular implants indicates that excessive growth of the adjacent cells results again in a restriction of the vessel particularly at the ends of the implants which results in reduced effectiveness of the implants. If a vascular implant is inserted into a human artery for the elimination of an arteriosclerotic stenosis, intimahyperplasia will occur within a year at the ends of the vascular implant and results in renewed stenosis. Upon infiltration of vessel systems with carcinoma cells, for example in the gall passage with a gall passage carcinoma, the vascular implant is rapidly overgrown by tumor cells.

EP 04 33 011 discloses a radioactive vascular implant for subjecting the adjacent tissue to radiation after implantation into a vessel. With such a vascular implant, cell growth in the adjacent tissue can be effectively reduced in the first few months after implantation.

The vascular implant consists preferably of a metal made radioactive by the addition of an isotope converted into a radionuclide by subsequent irradiation or by plating the radionuclide species onto a core structure. The radionuclide species should have a half life (t1/2) in the range of 7 hours (h) to 100 days (d). It is pointed out that the preferred radionuclide species were phosphor-32 (t1/2=14.3 d), vanadium-48 (t½=16 d) and gold-198 (t½=2.7 d). During their decay, these species of radio nuclides emit β-radiation and become the stable daughter nuclides sulfur-32, titanium-48 and mercury-198, so that the radioactivity practically disappears at the latest (in the case of $^{48}V$ which has the longest half life) after 5.5 months (the span of 10 half lives).

EP 0 539 165 A1 proposes to insert such a radioactive vascular implant into the gall passage in order to prevent the growth of malignant cells in the gall passage. For this purpose, the half life of the isotope is preferably between 10 hours and 1000 days.

It has been found, however, that, after the fading of the radioactivity even after longer periods (up to two years and more), cell growth and, consequently, intimahyperplasia and renewed stenosis may still occur. It would be possible to counter this in accordance with the cited reference by using radionuclides with a long half life for example radionuclides which have a half life of up to 100 days. Vascular inserts with such radionuclides however, would subject a patient to excessive radioactivity which is not tolerable since the radioactivity present at the beginning subsides only slowly. In addition, the intensity distribution over time is quite unfavorable in this case. It has been found that, in order to prevent imtimahypoplasia and a renewed stenosis, it is necessary to provide for a relatively high radiation intensity immediately after the implantation, but only a very small radiation intensity over an intermediate and longer period.

Such a radiation intensity distribution cannot be achieved with radionuclides with a medium half life.

With regard to the manufacture of a metallic radioactive vascular implant, the reference states that such an "element" is admixed to the metal which can be converted into a radioisotope. Additionally, implants with a radioactive coating are described. No further information concerning the manufacturing process are contained in the reference. It is also pointed out that, with implants with radioactive coatings, the coatings may come off and may be distributed throughout the body.

It is the object of the present invention to provide a radioactive vascular implant for placement into veins or arteries which does not have the disadvantages of the prior art implants as pointed out above. The implant should be such that it subjects the tissue to radiation for the whole period in which renewed stenosis could be expected and that the radiation is relatively high for a short period after the implantation, but is relatively low thereafter and over the long term.

SUMMARY OF THE INVENTION

In a vascular implant for the prevention or elimination of vascular restrictions a tubular body to be inserted into a body vessel includes at least a first nuclide species, which has a half life in the range of 7 hours to 7 days and a second nuclide species which has a half life of more than 100 days. Instead of providing a second nuclide species, the first nuclide species may be selected so that it decays into the second nuclide species thereby providing a high initial radioactivity for a relatively short period and a relatively low radioactivity over a relatively long period.

Of the two species of radionuclides, the short-lived radionuclide must be present already at the time of implantation. The long-lived radionuclide species can be generated in the vascular implant before the implantation together with the short-lived species, but preferably the short-lived radionuclide is selected such that it decays directly or indirectly into the long-lived radionuclide species.

The type and the concentration of the two radionuclide species is preferably so selected that, within the first three days after implantation of the vascular implant, at least 40% of the total activity is released. The total activity should preferably be in the range of 3 to 0.3 Mbq.

Particularly suitable radionuclide species with a short half-life are manganese-52 (t½=5.7 d), cobalt-55 (t½=0.73 d), Technetium-96 (t½=4.3 d), molybdenum-99 (t½=66 h) and nickel-57 (t½=36 h). Further usable are tantalum-182 (t½=5 d) and rhenium-182 (t½=13 h). If the short-lived radionuclide species as well as the long-lived species with half lives of more than 100 days are generated before the implantation, the long-lived species may include the nuclides cobalt-57 (t½=272 d), iron-55 (t½=2.7 a (years)) and zinc-65 (t½=244 d).

As mentioned, the short-lived radionuclide species is preferably so selected that it decays directly or indirectly into a radionuclide with a half-life of more than 100 days. Such short-lived species are cobalt-55, which decays into the daughter nuclide iron-55, rhenium-181 (t½=121 d) which decays into wolfram-181 (t½=121 d) and nickel-57 which forms cobalt-57 (t½=271 d). By selecting this type of short-lived radionuclide species, the manufacture of the vascular implants is substantially simplified since only one nuclide species has to be generated by irradiation.

Particularly preferred as short-lived radionuclide species is cobalt-55, which can be generated in iron-containing steels by deuterium irradiation. Cobalt-55 decays by capturing electrons, while emitting a soft x-ray radiation, into iron-55 which has a half life of 2.7 years.

Since for medical implants, nickel/titanium alloys and iron- and/or nickel containing steels, particularly the stainless steel CrNi 316 L, are utilized anyhow, the implants according to the invention can be made from commercially available iron-containing implants by subjecting the implant to deuterium irradiation to generate in the implant the short-lived radionuclide species cobalt-55. The short-lived radionuclide species nickel-57 is obtained by proton irradiation of nickel containing steels [Ni-58(p,pm) Ni-57]. In this case, a special manufacture of implants from irradiated radioactive materials is not necessary.

Vascular implants may also be made from tantalum alloys which are subsequently irradiated: If the short lived radionuclide species rhenium-181 is utilized, tantalum implants may be utilized, since rhenium-181 can be generated from tantalum-181 by a ($\alpha$,4 n) reaction.

Vascular implants with the above mentioned radionuclides, particularly with cobalt-55 as short-lived radionuclide species and its daughter nuclide iron-55 or with the short-lived nickel-57 and its daughter nuclide cobalt-57, have another important advantage: They decay by capture of electrons and emission of soft x-rays which, like $\beta$-radiation, has a penetration depth in the body of only a few millimeters, but which, unlike $\beta$-radiation, is not absorbed by the thrombosis-preventing coatings generally applied to the implants.

In some cases, it is appropriate to utilize, in addition to the radionuclide species mentioned, an other species which has a half-life in an intermediate range of 20 to 100 days. For this purpose, the nuclide cobalt-56 (t½=78 d), cobalt-58 (t½=71 d), or chromium-51 (t½=28 d) may be utilized. With three nuclides, the dosage intensity distribution over time can be particularly well adjusted to the requirements. The radionuclide species with the intermediate half life may also be generated either directly before the implantation or the short-lived nuclides are so selected that a direct or indirect daughter nuclide with intermediate half life is generated by the decay of the short-lived nuclide.

EXPLANATION OF THE INVENTION ON THE BASIS OF EXAMPLES

Example 1

Manufacture of a Vascular Implant

A commercially available segmented stent of stainless steel CrNi 316 L was irradiated. The length of the stent was 15 mm, the outer diameter was 1.6 mm (expandable to 6 mm) and the material thickness was 0.076 mm. For activation, the stent was placed into the external beam of a cyclotron with a 9.2 MeV deuteron flow. For this purpose, the stent was held in a miniature receptor of a motion machine and arranged and moved in the oriented deuteron beam by way of the highly precise positioning and adjustment equipment of a mechanical irradiation arrangement such that an evenly distributed homogeneous radioactivity was generated in the stent. The energy and type of radioactive particles were so selected that, in the CrNi-steel, the highest possible part of radio nuclides with electron capturing transitions ($\epsilon$) and the soft x-ray radiation (K$\alpha$,$\beta$=5 to 6 K$_e$V) resulting therefrom, as well as $\beta^+$ transitions were induced. This type of radiation provides for the desired near effectiveness (0.1 to 6 mm) in the tissue surrounding the stent.

The radio nuclide mixture generated thereby and its effects on the cellular tissue directly surrounding the stent are represented in Table 1.

The desired high initial intensity (48% of the total activity) in the first three days after implantation of such a stent is achieved by the generation of Co-55 (41%) and Tc-95 (7%). The nuclides Mn-52, Tc-96, Mo-99 with an activity contribution of together 24% provide for sufficient radioactivity over the next 2 to 3 weeks. Sufficient intermediate effectiveness over a period of about 250 days is achieved by the nuclides Co-56 and Co-58. Fe-55 (the daughter nuclide of Co-55) and Co-57 provide for a long term (up to about 9 years) irritation reduction in the surrounding tissue.

Example 2

Manufacture of a Vascular Implant

The sample as described in example 1 was re-done with the same commercially available stent under analogous conditions, but it was irradiated with a 30 MeV- proton beam.

The radionuclide mixture, as compared to the nuclide mixture obtained in example 1 has a 100% higher effectiveness on the tissue in the near range (0.1 to 6 mm) around the stent since the x-ray radiation and $\beta^+$ energies are substantially lower.

Example 3

Animal Tests

A stent activated in accordance with example 1, was implanted in animal tests into the arteries of New Zealand White Rabbits. The rabbits, which had a weight of 2.5 to 3 kg, were subjected to narcosis; a stent was implanted in each of the leg arteries, a non-activated stent into one leg and a stent activated in accordance with example 1 into the other.

Three rabbits were observed for 4 weeks and an additional three rabbits were observed for 12 weeks. After 4 and 12 weeks, respectively, the arteries were removed. They were fixed with formalin and subsequently embedded in Epoxy-resin. With a diamond coated saw blade, the vessels were then cut, together with the stents, into 50 µm thick vessel cross-sectional slices and the slices were colored by toluidene-blue.

The colored cross-sectional slices were examined under a light microscope and the dimensions of the tissue portions (intimahyperplasia, tissue growth) were determined quantitatively by a computer program, wherein six slices of the activated stents and six slices of the control stents were measured out and the data added up.

The average values and the standard deviation of the data of the altogether 12 vessels provided with stents resulted in the following values:

| Tissue Growth (Intimahyperplasia in mm²) | | |
|---|---|---|
| | After 4 Weeks | After 12 Weeks |
| Activated Stents | 0.2 ± 0.03 | 0.1 ± 0.04 |
| Control Stents | 1.0 ± 0.2 | 0.9 ± 0.1 |

The differences are statistically significant and clearly show that excessive undesired tissue growth, that is intimahyperplasia, as represented by the control stents can be prevented by the use of activated stents. In this connection, it is pointed out that the effective radiation is essentially a soft x-ray radiation. The values obtained for the control stents are essentially the same as obtained in earlier test series. The blood composition was found to be unaffected by the activated stents, that is, the anti-proliferatory effects of the activated stents were locally limited. The surrounding tissue such as the bladder and intestinal tissue remained unchanged. No activity was found in the excrement. Because of the gamma portion of the radiation, the activated body and represented in an image in the body and represented in an image. A change of the stent material as a result of the reactivity, will not occur because of the extremely low radionuclide atom content of at most $10^{-10}$.

hours to 7 days and which decays into at least one daughter radionuclide with a half life of more than 100 days.

2. An implant according to claim 1, wherein said radionuclide and/or said daughter nuclide emits soft x-ray radiation.

TABLE 1

| Radio Nuclide | Activity Generated in Mbq (%) of Total Activity | Half Life | Effective Period* | Effective Radiation Type $\epsilon$ = Electron Capture with Resulting X-ray Radiation (x); $\beta^+$ = Positron Radiation |
|---|---|---|---|---|
| Co-55; | 1.25 (41%) | 17.5 h | 2.5 d | $\epsilon$ 21% × 6.5 KeV |
| Daughter | | | | $\beta^+$ 80% <1.5 MeV |
| Nuclide Fe-55 | 0.00094 (0.04%) | 2.7 a | 9 a | $\epsilon$ 100% × 6 KeV $\beta^+$ 0% |
| Mn-52 | 0.5 (16%) | 5.7 d | 20 d | $\epsilon$ 70% × 5.4 KeV $\beta^+$ 30% <.6 MeV |
| Co-57 | 0.39 (13%) | 272 d | 2.5 a | $\epsilon$ 100% × 6.4 KeV $\beta^+$ 0% |
| Co-56 | 0.32 (11%) | 78 d | 260 d | $\epsilon$ 80% × 6.5 KeV $\beta^+$ 20% <1.5 MeV |
| Tc-95 | 0.2 (7%) | 20 h | 2.8 d | $\epsilon$ 100% × 17.5 KeV $\beta^+$ 0% |
| Tc-96 | 0.13 (4%) | 4.3 d | 14 d | $\epsilon$ 100% × 17.5 KeV $\beta^+$ 0% |
| Co-58 | 0.12 (4%) | 71 d | 235 d | $\epsilon$ 85% × 6.5 KeV $\beta^+$ 15% <0.5 MeV |
| Mo-99 | 0.12 (4%) | 66 h | 9 d | $\epsilon$ 0% $\beta^+$ 100% <1.23 MeV) |

*The effective period is the decay time down to 10% of the original activity.

TABLE 2

| Radio Nuclide | Activity Generated in Mbq (%) of Total Activity | Half Life | Effective Period*) | Effective Radiation Type $\epsilon$ = Electron Capture with Resulting X-ray Radiation (x); $\beta^+$ = Positron Radiation |
|---|---|---|---|---|
| Co-55; | 1.25 (58%) | 17.5 h | 2.5 d | $\epsilon$ 21% × 6.5 KeV |
| Daughter | | | | $\beta^+$ 80% <1.5 MeV |
| Nuclide Fe-55 | 0.00094 (0.04%) | 2.7 a | 9 a | $\epsilon$ 100% × 6 KeV $\beta^+$ 0% |
| Ni-57 | 0.44 (20%) | 36 d | 5 d | $\epsilon$ 54% × 6.9 KeV $\beta^+$ 46% <0.8 MeV |
| Cr-51 | 0.20 (9%) | 27.7 d | 92 d | $\epsilon$ 100% × 4.9 KeV $\beta^+$ 0% |
| Mn-52 | 0.12 (6%) | 5.7 d | 20 d | $\epsilon$ 70% × 5.4 KeV $\beta^+$ 30% <0.6 MeV |
| Tc-95 | 0.06 (3%) | 20 h | 2.8 d | $\epsilon$ 100% × 17.5 KeV $\beta^+$ 0% |
| Co-56 | 0.05 (2.3%) | 78 d | 260 d | $\epsilon$ 80% × 6.5 KeV $\beta^+$ 20% <1.5 MeV |
| Tc-96 | 0.02 (0.09%) | 4.3 d | 14 d | $\epsilon$ 100% × 17.5 KeV $\beta^+$ 0% |
| Co-57 | 0.01 (0.5%) | 271 d | 2.5 a | $\epsilon$ 100% × 6.4 KeV $\beta^+$ 0% |
| Mo-99 | 0.006 (0.3%) | 66 h | 9 d | $\epsilon$ 0% $\beta^+$ 100% <1.23 MeV) |

*)The effective period is the decay time to 10% of the original activity.

What is claimed is:

1. A vascular implant for the prevention or elimination of vascular restrictions, comprising a tubular body including at least one radionuclide species which has a half life of 7 hours to 7 days and which decays into at least one daughter radionuclide with a half life of more than 100 days.

2. An implant according to claim 1, wherein said radionuclide and/or said daughter nuclide emits soft x-ray radiation.

3. An implant according to claim 1, wherein said radionuclide species consists of at least one of the group comprising cobalt-55, rhenium-181, and nickel-57.

* * * * *